US012687492B2

(12) United States Patent
Tsuboi et al.

(10) Patent No.: US 12,687,492 B2
(45) Date of Patent: Jul. 21, 2026

(54) COAL ANALYZER, COAL ANALYSIS METHOD, MIXED COAL PREPARATION METHOD, AND COKE PRODUCTION METHOD

(71) Applicant: JFE STEEL CORPORATION, Tokyo (JP)

(72) Inventors: Toshiki Tsuboi, Tokyo (JP); Shunichi Kamezaki, Tokyo (JP)

(73) Assignee: JFE STEEL CORPORATION, Tokyo (JP)

( * ) Notice: Subject to any disclaimer, the term of this patent is extended or adjusted under 35 U.S.C. 154(b) by 206 days.

(21) Appl. No.: 18/695,923

(22) PCT Filed: Sep. 20, 2022

(86) PCT No.: PCT/JP2022/034999
§ 371 (c)(1),
(2) Date: Mar. 27, 2024

(87) PCT Pub. No.: WO2023/054065
PCT Pub. Date: Apr. 6, 2023

(65) Prior Publication Data
US 2025/0116602 A1     Apr. 10, 2025

(30) Foreign Application Priority Data
Sep. 30, 2021     (JP) ................................. 2021-161012

(51) Int. Cl.
*G01N 21/55*          (2014.01)
*C10B 57/04*          (2006.01)
(Continued)

(52) U.S. Cl.
CPC ............. *G01N 21/55* (2013.01); *C10B 57/04* (2013.01); *C10L 5/04* (2013.01); *G01N 21/274* (2013.01);
(Continued)

(58) Field of Classification Search
CPC ...... G01N 21/55; G01N 21/274; G01N 21/84; G01N 33/222; G01N 2021/559;
(Continued)

(56) References Cited

U.S. PATENT DOCUMENTS 4,045,299 A * 8/1977 MacDonald .............. C10B 9/00
                                                    201/15
4,568,424 A * 2/1986 Bauer ..................... C10B 21/20
                                                    201/1
(Continued)

FOREIGN PATENT DOCUMENTS

CN          102297850 A      12/2011
CN          102928340 A      2/2013
(Continued)

OTHER PUBLICATIONS

Jan. 2, 2025 extended Search Report issued in European Patent Application No. 22875935.3.
(Continued)

*Primary Examiner* — Tarifur R Chowdhury
*Assistant Examiner* — Kemaya Nguyen
(74) *Attorney, Agent, or Firm* — Oliff PLC

(57) ABSTRACT

An information processing device including a target person information acquisition unit configured to acquire target person information about a target person, an exercise evaluation information acquisition unit configured to acquire exercise evaluation information indicating evaluation of an exercise of the target person, a storage unit configured to store a trained model that outputs instruction content in which, when the target person information and the exercise evaluation information are input, evaluation of exercise information of the target person is estimated to be improved, and a report output unit configured to input the target person information and the exercise evaluation information to the (Continued)

trained model and output an instruction report including the instruction content output from the trained model.

5 Claims, 7 Drawing Sheets

(51) Int. Cl.
|  |  |
|---|---|
| *C10L 5/04* | (2006.01) |
| *G01N 21/27* | (2006.01) |
| *G01N 21/84* | (2006.01) |
| *G01N 33/22* | (2006.01) |

(52) U.S. Cl.
CPC ........... *G01N 21/84* (2013.01); *G01N 33/222* (2013.01); *C10L 2290/24* (2013.01); *C10L 2290/60* (2013.01); *G01N 2021/559* (2013.01)

(58) Field of Classification Search
CPC .... G01N 1/286; G01N 1/32; G01N 2001/364; C10B 57/04; C10B 45/00; C10L 5/04; C10L 2290/24; C10L 2290/60
See application file for complete search history.

(56) References Cited

U.S. PATENT DOCUMENTS

| | | | | |
|---|---|---|---|---|
| 4,701,838 | A | * 10/1987 | Swinkels | G01N 21/35 |
| | | | | 201/4 |
| 5,841,882 | A | 11/1998 | Celeski | |
| 12,227,699 | B2 * | 2/2025 | Quanci | G05B 23/0232 |

FOREIGN PATENT DOCUMENTS

| | | | | | |
|---|---|---|---|---|---|
| CN | 111160064 | A | | 5/2020 | |
| CN | 111879732 | A | | 11/2020 | |
| CN | 112132078 | A | | 12/2020 | |
| CN | 112881306 | A | | 6/2021 | |
| JP | S50-112096 | A | | 9/1975 | |
| JP | S58-022940 | A | | 2/1983 | |
| JP | S58-035442 | A | | 3/1983 | |
| JP | S58-153144 | A | | 9/1983 | |
| JP | S61191943 | A | * | 8/1986 | |
| JP | S62-180752 | U | | 11/1987 | |
| JP | 2005-338011 | A | | 12/2005 | |
| JP | 2006-016417 | A | | 1/2006 | |
| JP | 2014218649 | A | * | 11/2014 | C10B 57/04 |
| JP | 2016-065821 | A | | 4/2016 | |

OTHER PUBLICATIONS

Jun. 2, 2023 Office Action issued in Taiwanese Patent Application No. 111137076.
Sep. 19, 2023 Office Action issued in Japanese Patent Application No. 2023-507326.
Nov. 8, 2022 Search Report issued in International Patent Application No. PCT/JP2022/034999.

* cited by examiner

FIG. 2

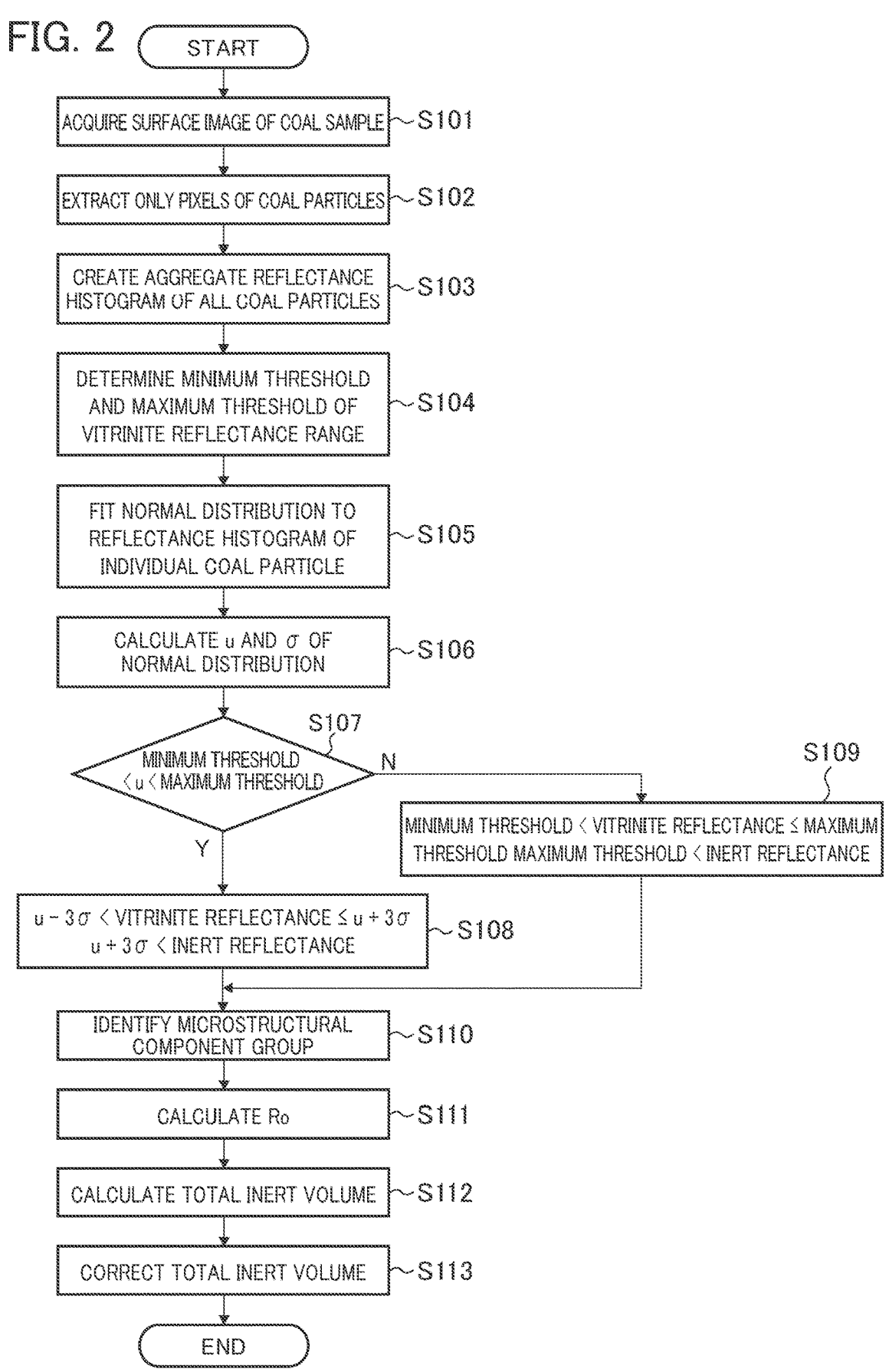

START

ACQUIRE SURFACE IMAGE OF COAL SAMPLE ～S101

EXTRACT ONLY PIXELS OF COAL PARTICLES ～S102

CREATE AGGREGATE REFLECTANCE HISTOGRAM OF ALL COAL PARTICLES ～S103

DETERMINE MINIMUM THRESHOLD AND MAXIMUM THRESHOLD OF VITRINITE REFLECTANCE RANGE ～S104

FIT NORMAL DISTRIBUTION TO REFLECTANCE HISTOGRAM OF INDIVIDUAL COAL PARTICLE ～S105

CALCULATE u AND $\sigma$ OF NORMAL DISTRIBUTION ～S106

S107

MINIMUM THRESHOLD < u < MAXIMUM THRESHOLD

N

S109

MINIMUM THRESHOLD < VITRINITE REFLECTANCE ≤ MAXIMUM THRESHOLD MAXIMUM THRESHOLD < INERT REFLECTANCE

Y $u - 3\sigma$ < VITRINITE REFLECTANCE ≤ $u + 3\sigma$
$u + 3\sigma$ < INERT REFLECTANCE ～S108

IDENTIFY MICROSTRUCTURAL COMPONENT GROUP ～S110

CALCULATE Ro ～S111

CALCULATE TOTAL INERT VOLUME ～S112

CORRECT TOTAL INERT VOLUME ～S113

END

COAL ANALYZER, COAL ANALYSIS METHOD, MIXED COAL PREPARATION METHOD, AND COKE PRODUCTION METHOD

TECHNICAL FIELD

The present invention relates to a coal analyzer, a coal analysis method, a mixed coal preparation method, and a coke production method.

BACKGROUND ART

Coke is produced from coal with various brands blended according to its product indexes.

Coal used for coke production is analyzed in advance for the structural components (Patent Literature 1).

CITATION LIST

Patent Literature

Patent Literature 1: JP S58-35442 A

SUMMARY OF INVENTION

Technical Problems

One of important product indexes of coke is cold coke strength.

There are three types of microstructural component groups (maceral groups) of coal: vitrinite, exinite, and inertinite. Among them, for example, inertinite is chemically inert and affects the cold coke strength.

For this reason, the ratio of inertinite (total inert amount) in coal used for coke production is measured.

Conventionally, the total inert amount of coal is measured using a microscope in accordance with JIS M 8816-1992 (Solid mineral fuels-Methods of microscopical measurement for the macerals and reflectance).

In this case, it is necessary to individually identify a microstructural component (maceral) belonging to inertinite such as semi-fusinite, thereby making the measurement very complicated. In addition, since the identification is performed based on a criterion such as a pattern, the identification result is largely dependent on a person, and such identification is also time-consuming.

The same applies to the measurement of the ratios of vitrinite and exinite, which are the other microstructural component groups.

The present invention has been made in view of the above points, and an object thereof is to easily obtain a ratio of at least one of the microstructural component groups of coal.

Solution to Problems

As a result of intensive studies, the present inventors have found that the above object is achieved by adopting the following constitution, and have completed the present invention.

That is, the present invention provides the following [1] to.

[1] A coal analyzer comprising: an image acquisition unit that acquires a surface image of a coal sample; an identification unit that identifies a microstructural component group included in the surface image; and a calculation unit that calculates a ratio of at least one of the microstructural component groups.

[2] The coal analyzer according to [1], wherein the identification unit identifies the microstructural component group based on a reflectance of the microstructural component group.

[3] The coal analyzer according to [1] or [2], wherein the calculation unit calculates an average reflectance Ro of vitrinite, which is one of the microstructural component groups.

[4] The coal analyzer according to any one of [1] to [3], wherein the calculation unit calculates a total inert amount that is a ratio of inertinite among the microstructural component groups.

[5] The coal analyzer according to [4], further comprising a correction unit that corrects the total inert amount.

[6] The coal analyzer according to [5], wherein the calculation unit calculates an average reflectance Ro of vitrinite, which is one of the microstructural component groups, and the correction unit corrects the total inert amount using the total inert amount and the average reflectance Ro of vitrinite.

[7] The coal analyzer according to [6], wherein the correction unit corrects the total inert amount using a multiple regression coefficient that is determined in advance, with the total inert amount and the average reflectance Ro of vitrinite as variables.

[8] A coal analysis method comprising: acquiring a surface image of a coal sample; identifying a microstructural component group included in the surface image; and calculating a ratio of at least one of the microstructural component groups.

[9] The coal analysis method according to [8], further comprising identifying the microstructural component group based on a reflectance of the microstructural component group.

[10] The coal analysis method according to [8] or [9], further comprising calculating an average reflectance Ro of vitrinite, which is one of the microstructural component groups.

[11] The coal analysis method according to any one of [8] to [10], further comprising calculating a total inert amount that is a ratio of inertinite among the microstructural component groups.

[12] The coal analysis method according to [11], further comprising correcting the total inert amount.

[13] The coal analysis method according to [12], further comprising: calculating an average reflectance Ro of vitrinite, which is one of the microstructural component groups; and correcting the total inert amount using the total inert amount and the average reflectance Ro of vitrinite.

[14] The coal analysis method according to [13], further comprising correcting the total inert amount using a multiple regression coefficient that is determined in advance, with the total inert amount and the average reflectance Ro of vitrinite as variables.

[15] A mixed coal preparation method comprising: blending multiple types of coals to prepare mixed coal; and identifying a total inert amount of at least part of the coal using the method according to any one of [8] to [14].

[16] A coke production method comprising using the mixed coal prepared by the method according to [15] to obtain coke.

Advantageous Effects of Invention

According to the present invention, the ratio of at least one of the microstructural component groups of coal can be easily obtained.

BRIEF DESCRIPTION OF DRAWINGS

FIG. 2 is a flowchart illustrating a flow of processing executed by respective units included in the coal analyzer.

DESCRIPTION OF EMBODIMENTS

[Coal (Microstructural Component and Microstructural Component Group)]

Coal is composed of microstructural components having different gloss and shape under a microscope.

A microstructural component (maceral) and a microstructural component group (maceral group) of coal will be described.

The microstructural component (maceral) of coal is a fine organic component of coal that is classified into 12 types with a microscope.

Specifically, the 12 types of microstructural components are telinite, collinite, degradinite, sporinite, cutinite, alginite, resinite, semi-fusinite, fusinite, micrinite, sclerotinite, and macrinite.

The microstructural component group (maceral group) of coal is a component group of microstructural components of coal having similar properties under a microscope, and is classified into three types.

Specifically, the three types of microstructural component groups are vitrinite, exinite, and inertinite (also referred to as "inert").

Microstructural components belonging to vitrinite are three types: telinite, collinite, and degradinite.

Microstructural components belonging to exinite are four types: sporinite, cutinite, alginite, and resinite.

Microstructural components belonging to inertinite are five types: semi-fusinite, fusinite, micrinite, sclerotinite, and macrinite.

In general, a total inert amount representing the ratio of inertinite among the three types of microstructural components (vitrinite, exinite, and inertinite) is used for the design of cold coke strength.

For this reason, the total inert amount of coal is obtained in the present embodiment.

[Coal Analyzer (Coal Analysis Method)]

Hereinafter, a coal analyzer of the present embodiment will be described with reference to FIGS. 1 to 10. The following description doubles as a description of the coal analysis method of the present embodiment.

<Configuration>

Figure 1:
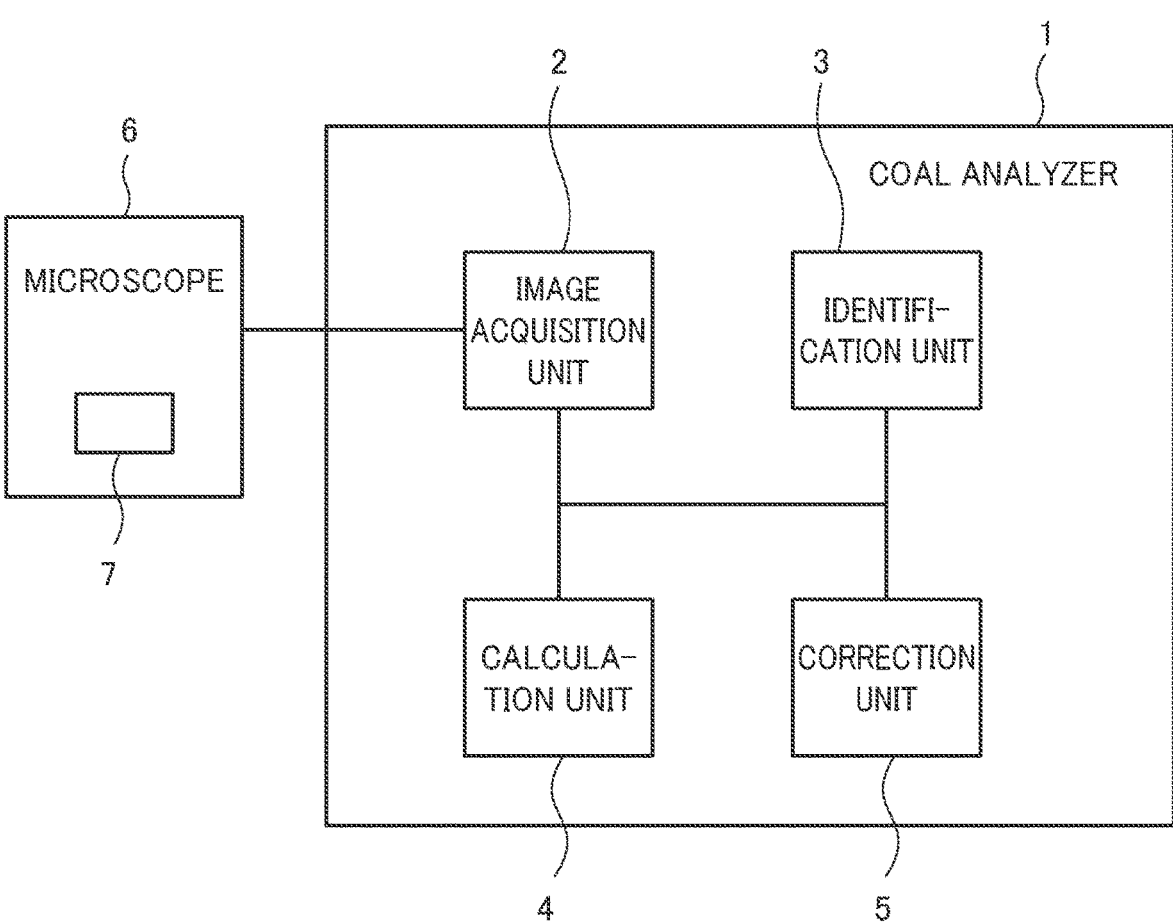
FIG. 1 is a block diagram illustrating a configuration of a coal analyzer.

FIG. 1 is a block diagram illustrating a configuration of a coal analyzer 1.

The coal analyzer 1 includes an image acquisition unit 2, an identification unit 3, a calculation unit 4, and a correction unit 5.

The image acquisition unit 2, the identification unit 3, the calculation unit 4, and the correction unit 5 are composed of, for example, a central processing unit (CPU), a main storage device such as a dynamic random access memory (DRAM) connected to the CPU, a mass storage device such as a solid state drive (SSD) or a hard disk drive (HDD) connected to the CPU, and a program for operating the CPU.

Processing executed by these units will be described later.

The coal analyzer 1 is connected to a microscope 6. A coal sample 7 is placed on a stage (not shown) of the microscope 6.

The coal sample 7 is prepared in accordance with JIS M 8816-1992.

More specifically, the coal sample 7 is obtained by pulverizing the collected coal, embedding the obtained coal particles in a resin, curing the resin, and then polishing the surface of the cured object.

The microscope 6 captures a surface image of the coal sample 7.

It is preferable that the microscope 6 has a function of designating a macro imaging range in advance, capturing a plurality of micro images while automatically moving the stage, and finally combining the captured micro images into a macro image.

In the present embodiment, for example, the size of the micro image is about 800 μm in length and 530 μm in width, and an oil immersion objective lens (magnification: 20 times) is used as the objective lens.

However, as long as the surface image of the coal sample 7 can be captured, the microscope 6 may not have the above function, and another objective lens may be used.

<Processing of Respective Units>

FIG. 2 is a flowchart illustrating a flow of processing executed by respective units included in the coal analyzer 1.

<<Image Acquisition Unit>>

First, the image acquisition unit 2 of the coal analyzer 1 causes the microscope 6 to capture a surface image of the coal sample 7, and acquires the captured surface image (step S101).

Only one surface image of the coal sample 7 may be captured to calculate the total inert amount, but only one surface image is merely part of the surface of the coal sample 7, and is thus less representative. To ensure the representativeness, it is preferable to image a plurality of portions of the surface of the coal sample 7, and it is more preferable to image all the portions of the surface (entire surface) of the coal sample 7.

In the present embodiment, the entire surface of the coal sample 7 is imaged to obtain about 2000 individual images, and the obtained individual images are combined to obtain one huge surface image.

Figure 3:
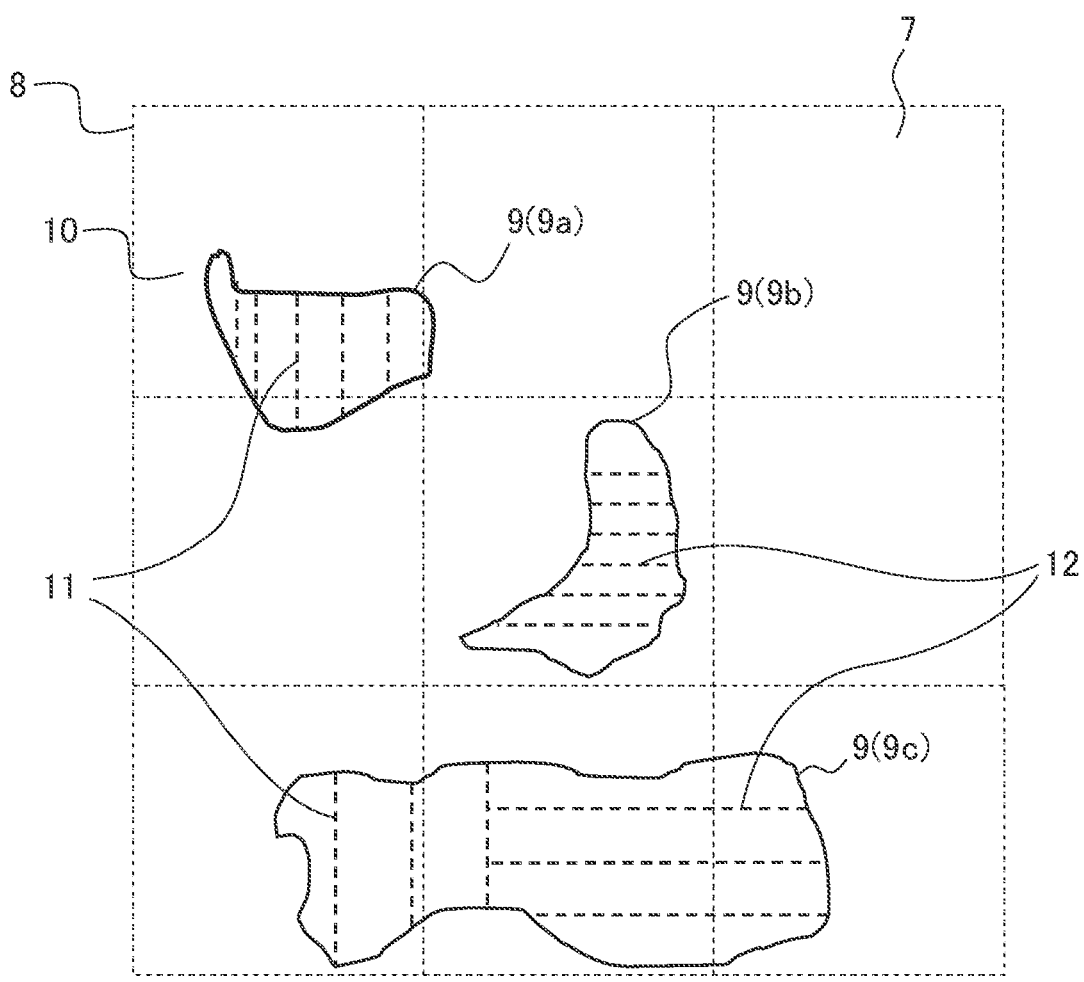
FIG. 3 is a view illustrating a surface image of a coal sample.

FIG. 3 is a view illustrating a surface image 8 of the coal sample 7. In FIG. 3, for simplification, nine individual images are combined to form one surface image 8.

In the surface image 8 of FIG. 3, three coal particles 9 (coal particle 9a, coal particle 9b, and coal particle 9c) embedded in the resin 10 are partly exposed.

In FIG. 3, vitrinite 11 is indicated by a vertical broken line, and inert 12 is indicated by a horizontal broken line.

The coal particle 9a in the upper part of the surface image 8 is formed of the vitrinite 11.

The coal particle 9b in the middle part of the surface image 8 is formed of the inert 12.

The coal particle 9c in the lower part of the surface image 8 is a mixture of the vitrinite 11 and the inert 12.

<<Identification Unit>>

Next, the identification unit 3 of the coal analyzer 1 extracts only pixels corresponding to the coal particles 9 from the surface image 8 (step S102).

In the surface image 8, the resin 10 takes on a blackish color. Thus, for example, the surface image 8 is subjected to differential processing, a boundary between the coal particle 9 and the resin 10, which has a large differential value, is detected, and only each pixel inside the boundary (that is, the coal particle 9) is acquired.

Each pixel constituting the surface image 8 includes luminance information.

In the present embodiment, a calibration curve between luminance and reflectance is created in advance using a standard test piece with known reflectance. The identification unit 3 of the coal analyzer 1 converts the luminance of each pixel into reflectance based on the created calibration curve. In this manner, the reflectance of each pixel of the coal particle 9 is obtained.

Next, the identification unit 3 of the coal analyzer 1 collects and aggregates the reflectances of the respective pixels to create an aggregate reflectance histogram of all the coal particles (step S103).

Figure 4:
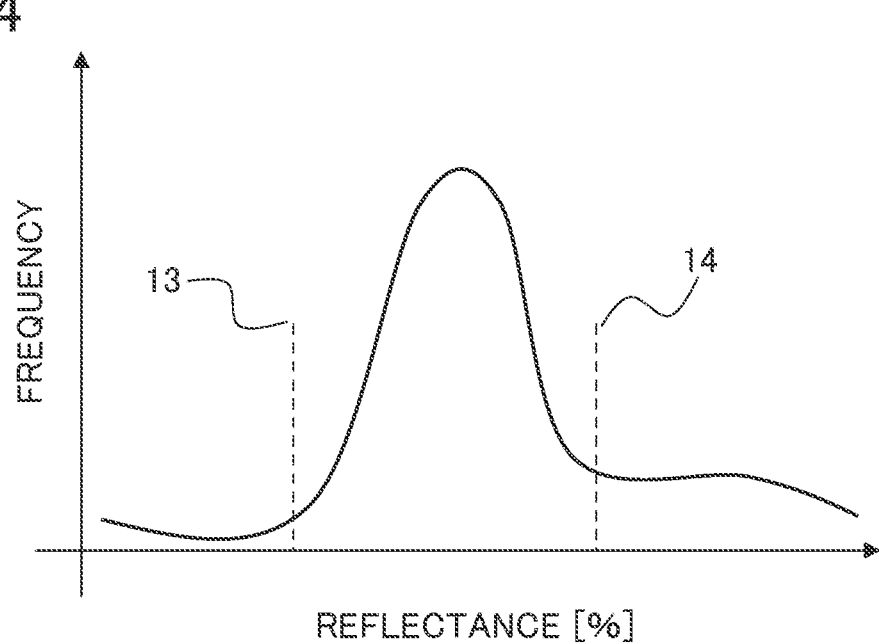
FIG. 4 is an aggregate reflectance histogram of all coal particles.

FIG. 4 is an aggregate reflectance histogram of all the coal particles. The horizontal axis represents reflectance (unit: %), and the vertical axis represents frequency (number of cases) (the same applies hereinafter).

The reflectances of vitrinite, exinite, and inert have a magnitude relationship: inert>vitrinite>exinite.

In general, the reflectance distribution of vitrinite is a normal distribution.

The histogram of FIG. 4 is formed by combining a mountain of vitrinite having a normal distribution shape with a mountain of inert having a long skirt in a brighter range (higher reflectance range).

It is assumed that exinite is negligible, since a ratio of exinite present is very low compared to vitrinite and inert.

In addition, in the present embodiment, the microstructural component group (vitrinite or inert) of the coal particle 9 included in the surface image 8 is identified based on the magnitude relationship in reflectance between vitrinite and inert. Specifically, the identification is carried out as follows.

The identification unit 3 of the coal analyzer 1 roughly determines the threshold of a vitrinite reflectance range in the aggregate reflectance histogram of all the coal particles. Specifically, as illustrated in FIG. 4, a minimum threshold 13 and a maximum threshold 14 of the vitrinite reflectance range are determined (step S104).

As a method of determining the thresholds, it is preferable to determine portions where the reflectance histogram changes rapidly as the thresholds. When this method is used, for example, the thresholds can be determined based on the differential value or the curvature of the reflectance histogram.

Next, the identification unit 3 of the coal analyzer 1 fits a normal distribution to the reflectance histogram of an individual coal particle (refer to FIG. 5 to be described later) on the assumption that the reflectance distribution of vitrinite is a normal distribution (step S105). The vitrinite reflectance range of the individual coal particle is thus determined.

Although the aggregate reflectance histogram of all the coal particles (refer to FIG. 4) may be used to determine the vitrinite reflectance range, the vitrinite reflectance range varies for each individual coal particle in reality. For this reason, determining the vitrinite reflectance range for each individual coal particle can make the finally obtained total inert amount more accurate.

Figure 5:
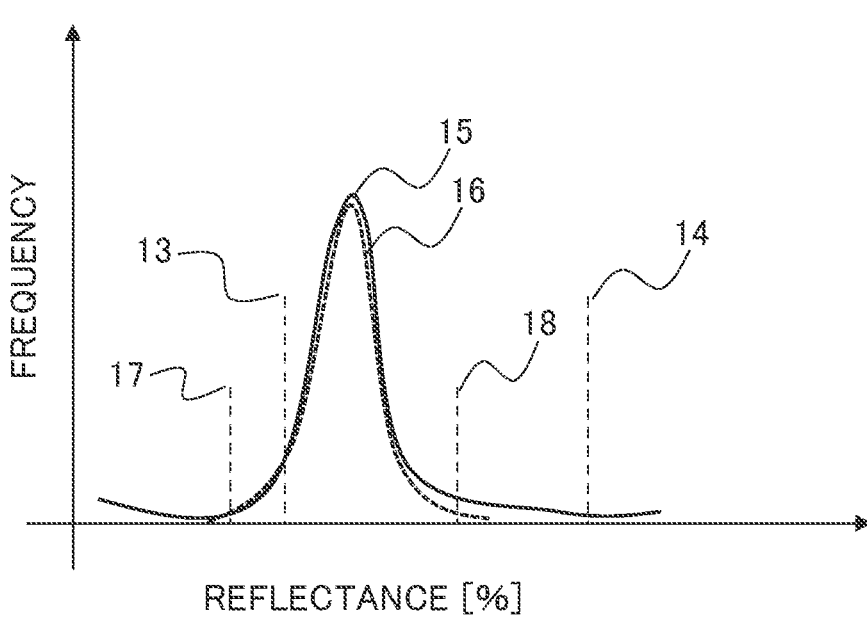
FIG. 5 is a reflectance histogram of one coal particle.

FIG. 5 is a reflectance histogram of one coal particle.

In FIG. 5, a normal distribution 16 is fitted to a reflectance histogram 15 of one coal particle. The identification unit 3 of the coal analyzer 1 calculates an average u and a standard deviation σ, which are parameters of the normal distribution 16 (step S106).

FIG. 5 illustrates a minimum value 17 and a maximum value 18 of the vitrinite reflectance. The minimum value 17 of the vitrinite reflectance is obtained from the formula "u−3σ". The maximum value 18 of the vitrinite reflectance is obtained from the formula "u+3σ".

FIG. 5 also illustrates the thresholds (minimum threshold 13 and maximum threshold 14) of the previously determined vitrinite reflectance range.

In a case where minimum threshold 13<u<maximum threshold 14 is satisfied (Y in step S107), the identification unit 3 of the coal analyzer 1 determines the vitrinite reflectance and the inert reflectance of the coal particle based on the following formulae (step S108).

$$u - 3\sigma < \text{vitrinite reflectance} \leq u + 3\sigma$$

$$u + 30 < \text{inert reflectance}$$

Then, the microstructural component group (vitrinite or inert) is identified based on the reflectance for each pixel (step S110).

On the other hand, in a case where minimum threshold 13<u<maximum threshold 14 is not satisfied (N in step S107), the identification unit 3 of the coal analyzer 1 determines the vitrinite reflectance and the inert reflectance of the coal particle based on the following formulae (step S109).

$$\text{Minimum threshold 13} < \text{vitrinite reflectance} \leq \text{maximum threshold 14}$$

$$\text{Maximum threshold 14} < \text{inert reflectance}$$

Then, the microstructural component group (vitrinite or inert) is identified based on the reflectance for each pixel (step S110).

The identification unit 3 of the coal analyzer 1 identifies a microstructural component group for each pixel of all the coal particles 9 included in the surface image 8 of the coal sample 7.

Reflectance outside the range of the above formulae is not considered.

<<Calculation Unit>>

Next, the calculation unit 4 of the coal analyzer 1 calculates the average reflectance Ro (unit: %) of vitrinite based on the following formula (step S111). Hereinafter, the "average reflectance Ro of vitrinite" is also simply referred to as "Ro". Ro represents the degree of maturation of coal.

$$Ro = \sum (\text{reflectance of vitrinite pixel})/\text{number of vitrinite pixels}$$

The "vitrinite pixel" means a pixel identified as vitrinite. In addition, an "inert pixel" means a pixel identified as inert.

Furthermore, the calculation unit 4 of the coal analyzer 1 calculates the total inert amount (unit: %) based on the following formula (step S112).

$$\text{Total inert amount} = 100 \times (\text{number of inert pixels})/$$
$$(\text{number of vitrinite pixels} + \text{number of inert pixels})$$

Also, when the ratio of the microstructural component group other than inertinite (for example, vitrinite) is calculated, it is obtained in the same manner as described above.

Here, a conventional method for obtaining the total inert amount will be described.

In the conventional method, in accordance with JIS M 8816-1992, the microstructural components of coal in the field of view are identified and counted based on a criterion such as a pattern while the stage of a microscope on which the coal sample is placed is manually moved at regular intervals.

Then, the total inert amount (unit: %) is obtained based on the following formula.

$$\text{Total inert amount} =$$
$$100 \times \{\text{coefficient } a \times \text{semi-fusinite (counted number)} +$$
$$\text{fusinite (counted number)} + \text{micrinite (counted number)} +$$
$$\text{sclerotinite (counted number)} + \text{macrinite (counted number)}\}/$$
$$(\text{total of counted numbers})$$

The coefficient a is 1 or $2/3$ in consideration of the active component of semi-fusinite. The calculation herein uses 1 as the coefficient a, but the present invention is not limited thereto.

In the conventional method, Ro is also manually obtained in the same manner as in the case of the total inert amount.

That is, in accordance with JIS M 8816-1992, the average reflectance of vitrinite is obtained by manually moving the stage of the microscope and identifying the vitrinite in the field of view.

In such a conventional method, microstructural components of coal need to be individually identified, thereby making the method very complicated. In addition, since the identification is performed based on a criterion such as a pattern, the identification result is largely dependent on a person, and such identification is also time-consuming.

Although a "computer" is used in the method described in Patent Literature 1, microstructural components such as semi-fusinite and fusinite belonging to inertinite are individually identified based on a criterion such as "fluctuation range of reflectance", which also makes the method complicated.

On the other hand, according to the coal analyzer 1 (coal analysis method) of the present embodiment, it is possible to easily obtain the total inert amount, which is the ratio of one type of microstructural components, without individually identifying the microstructural components of coal. At this time, since a criterion such as a pattern is not used, the analyzer can depend less on a person and also reduce the time.

<<Correction Unit>>

Next, the correction unit 5 of the coal analyzer 1 corrects the total inert amount calculated by the calculation unit 4 (step S113).

Here, the reason for performing the correction will be described.

Hereinafter, for the sake of convenience, Ro and the total inert amount obtained using the coal analyzer 1 (coal analysis method) of the present embodiment may be referred to as "Ro (automatic)" and the "total inert amount (automatic)", respectively.

In addition, Ro and the total inert amount obtained by the conventional method may be referred to as "Ro (manual)" and the "total inert amount (manual)", respectively.

The present inventors compared Ro (automatic) and the total inert amount (automatic) with Ro (manual) and the total inert amount (manual).

Ro (manual) and the total inert amount (manual) were obtained from observation results of arbitrary 100 fields of view and 250 fields of view, respectively.

Figure 6:
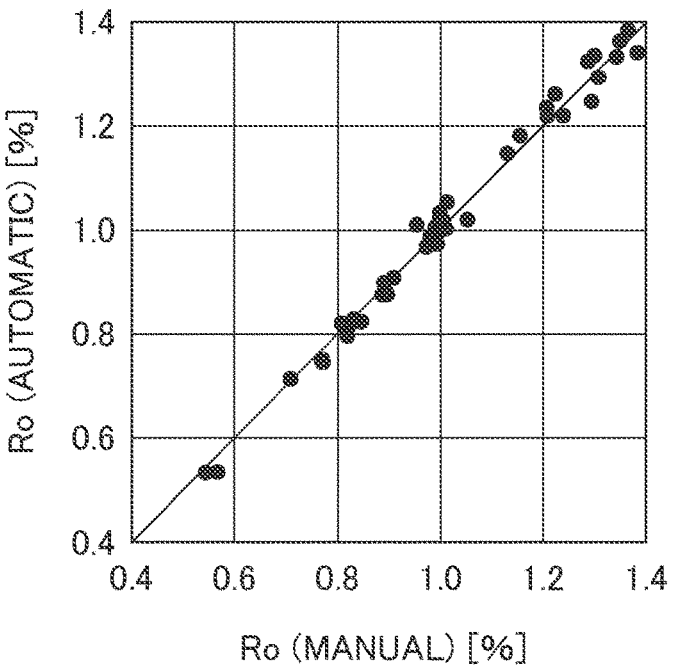
FIG. 6 is a relationship diagram between Ro (manual) and Ro (automatic).

FIG. 6 is a relationship diagram between Ro (manual) and Ro (automatic). The coefficient of determination $R^2=0.95$ and the error standard deviation RMSE=0.03% were found, and thus Ro (automatic) was equivalent to Ro (manual).

Figure 7:
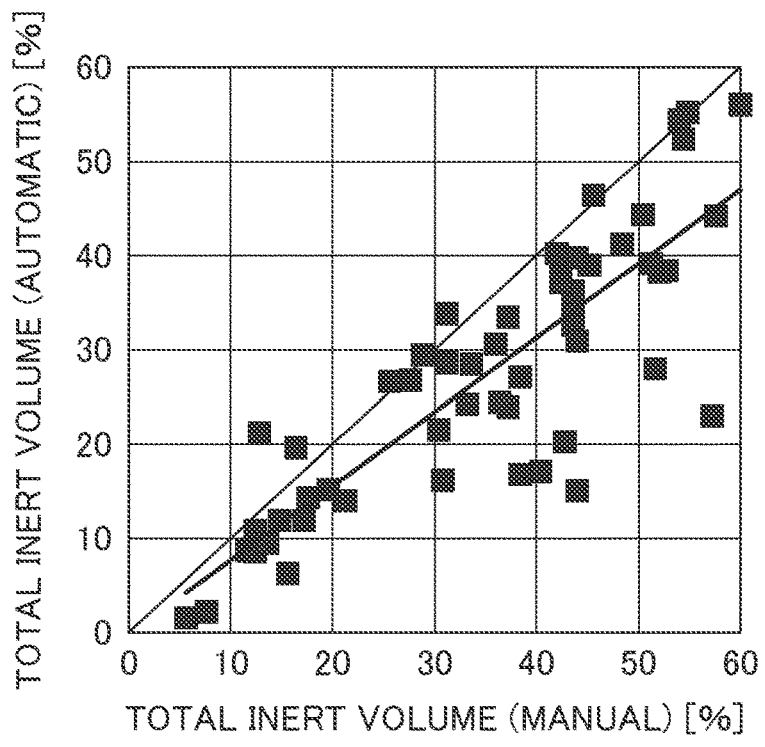
FIG. 7 is a relationship diagram between a total inert amount (manual) and a total inert amount (automatic).

FIG. 7 is a relationship diagram between the total inert amount (manual) and the total inert amount (automatic). The coefficient of determination $R^2=0.2$ and the error standard deviation RMSE=10% were found, and thus the total inert amount (automatic) tended to be underestimated in comparison with the total inert amount (manual).

In general, it is known that semi-fusinite belonging to inertinite has an intermediate property between vitrinite and inertinite.

Since the reflectance of semi-fusinite also indicates an intermediate value between those of vitrinite and inertinite, it is difficult to strictly classify semi-fusinite only by the magnitude of the reflectance value.

Figure 8:
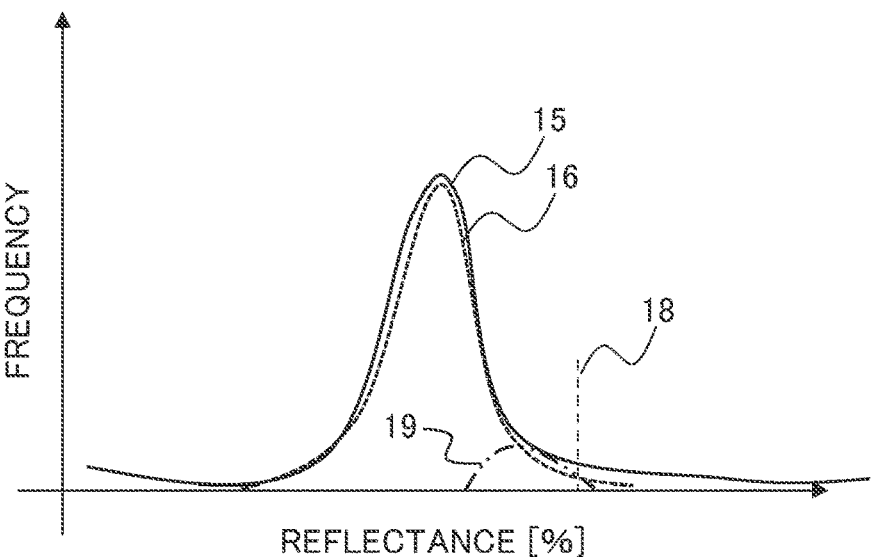
FIG. 8 is a reflectance histogram of one coal particle, which histogram illustrates a semi-fusinite reflectance.

FIG. 8 is a reflectance histogram of one coal particle, which histogram illustrates a semi-fusinite reflectance. In FIG. 8, the normal distribution 16 is fitted to the reflectance histogram 15 of one coal particle, and the maximum value 18 of the vitrinite reflectance is also indicated.

Furthermore, FIG. 8 illustrates a semi-fusinite reflectance 19 (a histogram of the semi-fusinite reflectance).

As illustrated in FIG. 8, the vitrinite reflectance range includes many semi-fusinite reflectances. In this case, since semi-fusinite belonging to inertinite is erroneously recognized as vitrinite, the total inert amount (automatic) is underestimated in comparison with the total inert amount (manual), as illustrated in FIG. 7. The present inventors considered as described above.

Accordingly, the present inventors obtained the ratio (unit: %) of semi-fusinite by the conventional method as in the case of the total inert amount. Hereinafter, this may be referred to as a "semi-fusinite ratio (manual)".

Figure 9:
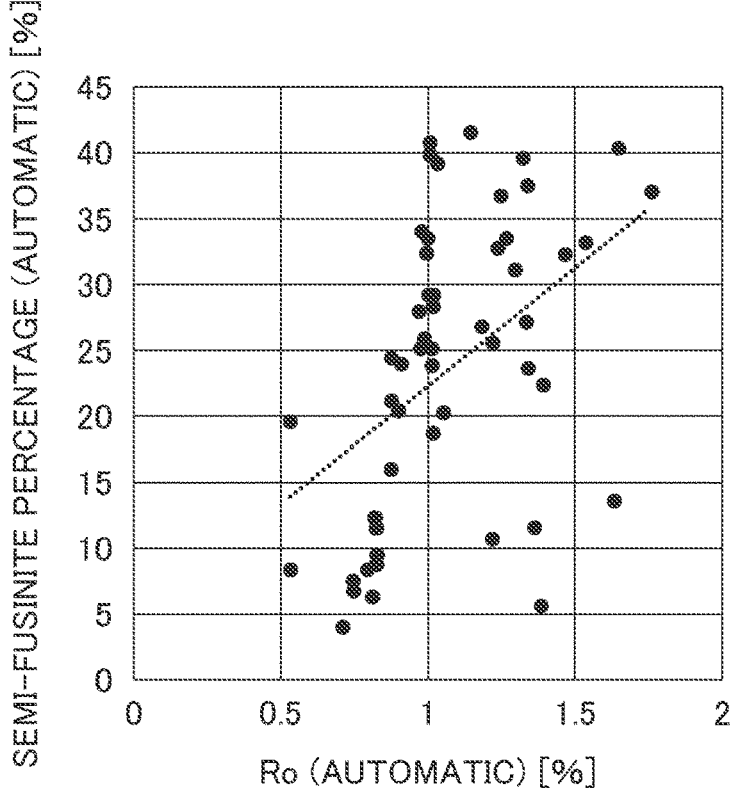
FIG. 9 is a relationship diagram between Ro (automatic) and a semi-fusinite ratio (manual).

FIG. 9 is a relationship diagram between Ro (automatic) and the semi-fusinite ratio (manual).

There is a correlation of the coefficient of determination $R^2=0.3$ between Ro (automatic) and the semi-fusinite ratio (manual), and as illustrated in FIG. 9, the semi-fusinite ratio (manual) increases as Ro (automatic) rises.

Based on FIG. 9 as described above, the present inventor considered that the influence of erroneously recognizing semi-fusinite as vitrinite when obtaining the total inert amount (automatic) can be corrected using Ro (automatic).

The present inventors performed multiple regression analysis on the total inert amount (manual) based on the following formula using two explanatory variables, Ro (automatic) and total inert amount (automatic).

Total inert amount (manual) =

$$\{a \times \text{total inert amount (automatic)}\} + \{b \times Ro \text{ (automatic)}\} + c$$

The multiple regression coefficients were a=0.92, b=24.1, and c=−15.9.

The present inventors corrected the total inert amount (automatic) using the multiple regression coefficients obtained by the multiple regression analysis.

Specifically, a corrected total inert amount (automatic) was obtained based on the following formula.

Corrected total inert amount (automatic) =

$$\{a \times \text{total inert amount (automatic)}\} + \{b \times Ro \text{ (automatic)}\} + c$$

Figure 10:
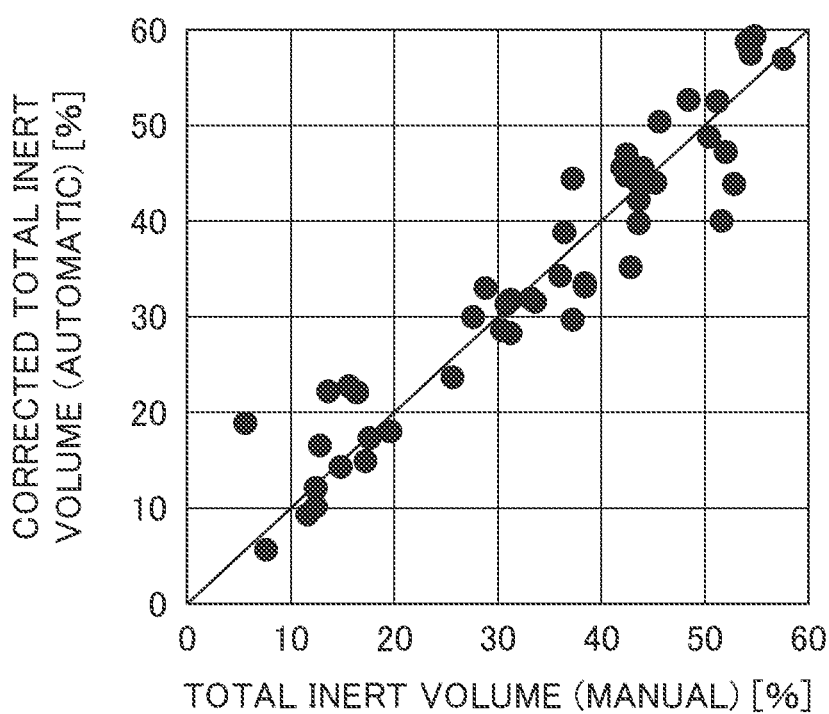
FIG. 10 is a relationship diagram between the total inert amount (manual) and a corrected total inert amount (automatic).

FIG. 10 is a relationship diagram between the total inert volume (manual) and the corrected total inert amount (automatic). The coefficient of determination $R^2$=0.9 and the error standard deviation RMSE=4% were found, and thus the corrected total inert amount (automatic) was equivalent to the total inert amount (manual).

If the total inert amount (manual) is more accurate than the total inert amount (automatic), it can be said that the corrected total inert amount (automatic) obtained by the correction using the multiple regression coefficient is also accurate.

Therefore, the correction unit 5 of the coal analyzer 1 determines and retains the multiple regression coefficient in advance.

Then, the total inert amount is corrected using the multiple regression coefficient as well as Ro (automatic) and the total inert amount (automatic) calculated by the calculation unit 4 (step S113).

Through such correction, the finally obtained total inert amount can be made more accurate.

Note that the explanatory variables in the multiple regression analysis are not limited to the two, i.e., Ro (automatic) and the total inert amount (automatic). Other information that can be acquired from the surface image 8 may be further added as an explanatory variable.

[Preparation of Mixed Coal and Coke Production]

Coke is produced from coal with various brands blended according to its product indexes.

That is, a plurality of types of coals are blended to prepare mixed coal, and the prepared mixed coal is calcined in a coke oven or the like to obtain coke.

At this time, it is preferable to identify the total inert amount of at least part of the coal to be blended using the coal analysis method of the present embodiment described above.

As described above, according to the coal analysis method of the present embodiment, the total inert amount can be easily obtained and the time can be shortened, and thus the preparation of mixed coal and coke production can also be simplified and expedited as a whole. In addition, the obtained total inert amount can be immediately reflected in coal blending calculation or the like.

REFERENCE SIGNS LIST

1: coal analyzer
2: image acquisition unit
3: identification unit
4: calculation unit
5: correction unit
6: microscope
7: coal sample
8: surface image
9 (9a, 9b, 9c): coal particle
10: resin
11: vitrinite
12: inert
13: minimum threshold in vitrinite reflectance range
14: maximum threshold in vitrinite reflectance range
15: reflectance histogram of one coal particle
16: normal distribution
17: minimum value of vitrinite reflectance
18: maximum value of vitrinite reflectance
19: semi-fusinite reflectance

The invention claimed is:

1. A coal analysis method comprising:
acquiring a surface image of a coal sample;
identifying a microstructural component group included in the surface image;
calculating a ratio of at least one of microstructural component groups;
calculating a total inert amount that is a ratio of inertinite among the microstructural component groups;
calculating an average reflectance Ro of vitrinite, which is one of the microstructural component groups;
correcting the total inert amount, after the total inert amount has been calculated from the surface image, using the total inert amount and the average reflectance Ro of vitrinite; and
blending multiple types of coals to prepare mixed coal based on the corrected total inert amount.

2. The coal analysis method according to claim 1, further comprising identifying the microstructural component group based on a reflectance of the microstructural component group.

3. The coal analysis method according to claim 1, further comprising correcting the total inert amount using a multiple regression coefficient that is determined in advance, with the total inert amount and the average reflectance Ro of vitrinite as variables.

4. A mixed coal preparation method comprising:
identifying a total inert amount of at least part of the coal using the method according to claim 1.

5. A coke production method comprising using the mixed coal prepared by the method according to claim 4 to obtain coke.

\* \* \* \* \*